United States Patent [19]

Robbins et al.

[11] Patent Number: 4,600,589
[45] Date of Patent: Jul. 15, 1986

[54] **MEAT TENDERIZATION WITH A PROTEOLYTIC ENZYME FROM *TRICHODERMA REESEI***

[75] Inventors: Frederick M. Robbins, Ashland, Mass.; Alfred L. Allen, Pascoag, R.I.; John E. Walker; Samuel H. Cohen, both of Framingham, Mass.

[73] Assignee: The United States of America as represented by the Secretary of the Army, Washington, D.C.

[21] Appl. No.: 663,516

[22] Filed: Oct. 22, 1984

[51] Int. Cl.$^4$ .......... A23L 1/31; C12N 9/58; C12N 1/14; C12R 1/885

[52] U.S. Cl. .......... 426/56; 435/223; 435/254; 435/815; 435/816; 435/945

[58] Field of Search .......... 426/56, 58, 59; 435/223, 254, 815, 816, 945

[56] References Cited

U.S. PATENT DOCUMENTS

| | | | |
|---|---|---|---|
| 2,963,376 | 12/1960 | Hogan et al. | 426/59 |
| 3,798,334 | 3/1974 | Earl et al. | 426/58 |
| 4,472,504 | 9/1984 | Gallo | 435/945 X |

FOREIGN PATENT DOCUMENTS

| | | | |
|---|---|---|---|
| 218988 | 1/1958 | Australia | 426/56 |
| 913202 | 12/1962 | United Kingdom | 426/56 |

OTHER PUBLICATIONS

Wang et al., Food Research, vol. 20, No. 6, 1955, pp. 587–597.

*Primary Examiner*—David M. Naff
*Attorney, Agent, or Firm*—Anthony T. Lane; Robert P. Gibson

[57] ABSTRACT

Meat is tenderized by adding thereto a proteolytic enzyme obtained by culturing the microorganism, *Trichoderma reesei* strain MCG 80. The enzyme is an aspartic acid protease with proteolytic properties similar to the animal protease, Cathepsin D. The enzyme acts selectively upon the myofibrillar proteins of meat producing a desirable uniform texture. Culturing of the microorganism in a medium containing glucose and lactose results in high enzyme yield.

6 Claims, No Drawings

MEAT TENDERIZATION WITH A PROTEOLYTIC ENZYME FROM *TRICHODERMA REESEI*

The invention described herein may be manufactured, used, and licensed by or for the Government for governmental purposes without the payment to us of any royalty thereon.

BACKGROUND OF THE INVENTION

This invention relates to proteolytic enzymes and to a method of producing such enzymes by culturing *T. reesei* MCG80 under suitable conditions. These enzymes have been found suitable for tenderizing animal muscle used for food purposes.

The increasing cost of animal meats for human consumption has heightened interest in the development of meat tenderizers which can improve the acceptability of lower grade meats. Protein chemistry is playing an increasingly important role in the development of methods for the selective tenderization of muscle used as food (meat, fish). At present, commercial meat tenderizers contain the plant protease papain which is relatively indiscriminate in its attack on muscle proteins and leads to extensive degradation of the structural proteins, myosin and actin as well as the other proteins associated with myofibrils.

Research into the post-mortem aging of bovine muscle has shown that there are two important phases which affect texture. The first, which is accompanied by a drop in adenosine triphosphate (ATP) concentration and a fall in pH from a physiological value of about 7.1 to about 5.3, results in rigor. This phase is complete in about two days with no significant change in muscle fiber surface ultrastructure occurring except shortening. The second stage of aging, the resolution of rigor, is noticeable in about five days. Transverse breaks appear in muscle fibers and elongation of sarcomere lengths occur with a decrease in tensile strength of fibers. At the myofibrillar level, Z—line degradation occurs and the interactions between actin and myosin weaken. This second stage of aging results in tenderization and has recently been shown to be due, in a large measure, to selective proteolysis of the muscle proteins by cathepsins, the endogenous proteolytic enzymes of muscle.

Cathepsin D, the major acidic proteolytic enzyme of muscle, has been shown to produce structural change in muscle under post-mortem conditions which were similar to those observed during aging. Treatment of bovine muscle with bovine spleen extract, a rich source of Cathepsin D, produced structural changes similar to those occurring during natural aging. The texture of the muscle treated with spleen extract was similar to that of naturally aged and tenderized muscle.

The presence of large amounts of connective tissue adversely affects the texture of meat. Since muscle has very little endogenous proteolytic activity against connective tissue, aging does little to improve the texture of muscle containing large amounts of connective tissue. Meat tenderizers containing papain possess significant activity against connective tissue or proteins which could be beneficial in modifying the texture of meat at high temperatures (55°–65°) but the indiscriminate proteolytic action of this enzyme on the myofibrillar proteins leads to overall inferior textural properties. By contrast, the spleen extract also has considerable activity against connective tissues but is quite selective in its action on the myofibrillar proteins. This recommends it both as a superior tenderizer for muscle and for upgrading inferior cuts of meat.

A disadvantage to the use of catheptic enzymes obtained from spleen is the difficulty of obtaining the enzyme at a reasonable cost in a reasonable yield. The production of similar enzymes from microbial sources could be an attractive solution to this problem by producing large quantities at low cost.

Interest has grown in the isolation and utilization of extracellular proteolytic enzymes from microbial sources as reagents in laboratory and clinical procedures and for industrial processing. These enzymes are of several types, including, serine proteases, metalloproteases and acid proteases.

This application describes the preparation, isolation and characterization of an aspartic acid protease from the fungus *Trichoderma reesei* with properties similar to the animal protease Cathepsin D. It also describes the use of the protease as a meat tenderizer and its use to increase the water absorbing capacity of stored freeze-dried meats.

SUMMARY OF THE INVENTION

According to the present invention, a proteolytic enzyme is produced by the growth of the fungus *Trichoderma reesei* MCG80 on a glucose-lactose culture medium. This enzyme is an aspartic acid protease with proteolytic properties similar to the animal protease Cathepsin D. It may be readily isolated and purified from the culture filtrate through acetone fractionation and affinity chromatography. The enzyme produced selectively broke down a myofibril suspension and was shown to degrade the chains of beef intramuscular connective tissue. The advantage of the enzyme was it was found to work selectively upon the myofibrillar proteins, producing a desirable uniform texture, not the objectionable "mushy" structure which is often the result of the use of tenderizers like papain.

DETAILED DESCRIPTION

The proteolytic enzyme of this invention is an aspartic acid protease obtained by the culturing of the fungus *Trichoderma reesei* and having properties similar to the animal protease Cathepsin D. The enzyme is produced in high yield by the organism when grown on a glucose-lactose culture medium. It is readily isolated and purified from the culture filtrate.

The specific organism found to produce an optimum quantity of enzyme was *Trichoderma reesei* MCG80. This strain was produced from parent strain RUT C30 as described in U.S. Pat. No. 4,472,504. *T. reesei* strain MCG80, the microorganism used in this application, is the same microorganism deposited as a culture in the Agricultural Research Culture Collection of the U.S. Department of Agriculture, Peoria, Ill.

In connection with the filing of the patent application which has issued as U.S. Pat. No. 4,472,504, *T. reesei* strain MCG80 has been made permanently available to the public through the Agricultural Research Culture Collection of the U.S. Department of Agriculture.

In terms of its morphology, strain MCG80 is classified as a semiparamorphic mutant, which shows restricted distal growth on potato dextrose agar (PDA) plates and, in this manner, is similar to *T. reesei* strain MCG77. It does not spread rapidly over media surfaces as do other non-paramorphic strains of *T. reesei*. On PDA medium, strain MCG80 does, however, conidiate poorly and forms a compact mycelial colony. Strain MCG80 is best distinguished from other mutant strains MCG77 and RUT-30, in the amount of extracellular cellulase/soluble protein it can produce when grown on cellulase inducing substrates and by the rate at which cellulase/soluble protein is produced. In U.S. Pat. No. 4,472,504, the inducibility of MCG80 by cellulose and cellulose hydrolyzate sugars is discussed as well as its inducibility of lactose. The ability to recognize inducer analogs such as lactose offers a number of methodological advantages. The ability to work with soluble materials in the fermentation reduces engineering problems associated with insoluble substances in a fermentation.

EXAMPLE 1

The stock cultures of Trichoderma reesei MCG80 (hereinafter referred to as MCG80) were maintained on potato dextrose agar slants at 24° C. In the fermenter cultures, the basic salts medium used was that described by Mandels and Reese, Journal of Bacteriology,Volume 73, p. 269 (1957) except that urea and proteose peptone were not added and the salts were present at twice the reported concentration. Tween 80 (Sigma Chemical Co., St. Louis, Mo.) was present at a concentration of 0.01%. Fermenter cultures were spore inoculated. All experiments were carried out in a 14 liter Magnaferm fermenter (New Brunswick Sci., New Brunswick, N.J.). The pH was maintained at 3.5 by the addition of 2N ammonium hydroxide. The temperature of the fermentation was kept at 28° C. Carbon dioxide was measured in the exit gas with a Lira Model 303 infrared analyzer (Mine Safety Products Co., Pittsburgh, Pa). Foaming was prevented by continuous addition of silicone antifoam SAG-100 (Union Carbide Corp., Tarrytown, N.Y.). The fermentations were carried out under carbon limitation using a fed batch technique as described by Allen, A. L., Biotechnology Bioengineering Symp. No. 13, Wiley-Interscience, New York, page 451 (1983). The carbohydrate feed (50% water/volume solution) was controlled in order to maintain carbon limitation and to control growth.

The fermentations were started with 2% lactose and a two-fold concentration of standard salts as described above. After the lactose was consumed, the 50% carbohydrate syrup was fed in intermittently using the carbon dioxide level in the exit gas for feed back control. The exit gas level of carbon dioxide was used as an indicator of biomass concentration. Feed rate was determined and regulated using a computer, so that the level of biomass could be controlled. The biomass concentration was raised to the desired level of feeding in a 50% syrup at a rate corresponding to the maintenance level (as determined by carbon dioxide evolution) of the desired biomass concentration. The syrup contained 25% w/v glucose (Fisher Scientific, Fair Lawn, N.J.) and 25% w/v lactose in an aqueous solution. The carbohydrate feed was controlled to maintain a constant evolution of carbon dioxide (16 millimoles of carbon dioxide/liter/hour). After 6 days maintaining the constant evolution of carbon dioxide and biomass (17 g/l ), the production of the measured extracellular enzymes ceased, at which time the contents of the fermenter were harvested. An aliquot sample of the culture was taken and passed through a fiberglass filter to remove the microorganisms from the culture. The resultant culture filtrate containing acid protease was employed in the following examples.

Several methods were used to obtain a fungal enzyme preparation. Acetone fractionation was performed on the culture filtrate to obtain a purer protease sample. 1100 ml of acetone at 4° C. was added to one liter of culture filtrate and the mixture allowed to stand overnight at 4° C. The majority of the supernatant was decanted and the remaining precipitate was recovered by centrifugation, air dried and then dried in vacuo. The majority of protease activity was recovered in the precipitate. Affinity chromatography was used to further purify the acetone precipitated protein. The affinity chromotography was carried out using pepstatin agarose (Pierce Chemical of Rockford, Ill.) 500 mg of the acetone precipitation protein was dissolved in 25 ml pH 3.2, 0.05M citrate buffer containing 0.6M naCl and applied to a column of the affinity gel made up in the same buffer. The gel was then washed with the citrate buffer until the optical density (O.D.) of the effluent at 280nm was essentially zero. The bound enzyme was eluted from the affinity column using pH 8.6 0. 1M tris (hydroxymethyl) aminomethane (TRIS) as the elution buffer.

Protease activity was determined using acid denatured hemoglobin as substrate at pH 3.5 as described by Keilova and Tomasek, Coll. Czech. Chem. Commun. Vol. 41, p 2440, 1976. One unit of activity corresponds to an absorbance increase at 280 nm of 1.00/minute at 37° C.

The result of the acetone fractionation with the addition of 1.1 volumes of acetone to the crude culture filtrate was the precipitation of approximately 93% of the acid protease with a 4-fold increase in specific activity. The total activity recovered in the acetone precipitate was greater than 100% of the apparent activity present in the original culture filtrate, indicating that the procedure was probably removing inhibitors of the acid protease. The acetone precipitated protease fraction was further fractionated on a pepstatin-agarose affinity column. The protease fraction was applied to the column in pH 3.2 0.05M citrate buffer containing 0.6 MNaCl and washed with the buffer until the O.D. 280 nm of the effluent was below 0.1. This unbound breakthrough fraction had none of the acid protease activity, but was found to contain all of the carbohydrate and cellulase activity associated with the acetone precipitated fraction. 93% of the protease activity was recovered with a 3-fold increase in specific activity when the column was eluted with the pH 8.6 TRIS buffer.

Our experiments demonstrate that acid proteases are present at high levels in culture filtrates of Trichoderma reesei MCG80 grown on glucose/ lactose and can be readily purified and recovered in good yields by simple acetone precipitation followed by affinity chromatography on a pepstatinagarose column. The properties of the protease (i. e. inhibition by pepstatin and pH activity optimum) indicate that it belongs to the aspartic acid carboxyl proteinase class, which includes cathepsin D and pepsin. The ready availability of this protease indicates that it has potential commercial application. In this regard, several experiments were performed to evaluate the potential use this protease may play in meat processing as a tenderizer. The following examples illustrate the use of this protease as a meat tenderizer, especially when compared to current commercial tenderizers.

EXAMPLE 2

The action of the enzyme obtained according to the process described in Example 1 was tested on a beef myofibrial suspension containing 1.5 mg/ml protein. 0.1 ml of fungal enzyme preparation (culture filtrate) containing 0.3 hemoglobin activity units per ml was added to 0.5 ml of a beef myofibril suspension in 0.01 M Na phosphate 0.15 M Na Cl—0.02% Na azide pH 5.34 buffer and allowed to stand at room temperature for eighteen hours. A myofibril sample containing no enzyme was treated in an identical fashion. Each sample was examined by sodium dodecyl sulfate—polyacrylamide gel electrophoresis. Compared to the untreated sample, which showed no degradation, the enzyme treated sample showed degradation of the heavy chain of myosin (200,000 daltons) to fragments in the range from less than 200,000 daltons to about 100,000 daltons. Little or no breakdown of actin was evident, however, there appeared to be some degradation of the troponin components with molecular weights in the range of 37,000 to less than 20,000 daltons.

EXAMPLE 3

0.1 ml of fungal enzyme preparation obtained as described in Example 1 (0.3 units hemoglobin activity per ml) was added to 0.5 ml of a beef intramuscular connective tissue (IMCT) slurry (1.18 mg protein per ml) made up in 0.01 M Na phosphate, 0.15 M NaCl, 0.02% Na azide pH 5.5 buffer. The mixture was allowed to stand overnight (18 hours) at room temperature. A control sample containing no enzyme was treated similarly. These samples were examined by sodium dodecylsulfate-polyacrylamide gel electrophoresis, and showed that the treatment with fungal enzyme results in a degradation of the highly crosslinked gamma collagen chains of IMCT, as well as the beta (dimer) and alpha (monomer) chains of IMCT while the control sample showed no degradation. These results demonstrate the selectivity of this enzyme and its usefulness in meat processing.

EXAMPLE 4

To test the effectiveness of the fungal protease in tenderizing beef muscle, the enzyme was evaluated using flaked and formed beef steaks prepared as described by Cohen et al in Food Microstructure, Vol. 1, p. 99 (1982). The steaks were prepared from utility grade beef by mixing the freeze dried enzyme into the flaked meat which contained no salt or sodium tripolyphosphate. The steaks had an enzyme content of 1.00 gm (1,000 units)/10 lbs. of beef. Similar steaks containing no added enzyme were also prepared for comparison testing. After preparation, the steaks were stored at 0° F. for five months before shear testing using the punch and die method described in U.S. Pat. No. 4,007,632. The maximum shear stress and stiffness values of the samples represent the average of 24 measurements on 8 steaks and are shown in Table 1.

TABLE 1

| Sample | Max. Shear Stress (Newtons/cm$^2$) | Stiffness (Newtons/cm$^2$) |
| --- | --- | --- |
| No enzyme (control) | 18.20 ± 6.91 | 13.83 ± 4.19 |
| Enzyme-treated | 14.36 ± 2.94 | 9.08 ± 2.57 |

The results of these experiments show that the extracellular proteases present in culture filtrates of the fungus *T. reesei* are quite similar to Cathepsin D in their action on the myofibrillar proteins and that they are also capable of degrading highly crosslinked IMCT. The shear stress value for the enzyme-treated flaked and formed beef was significantly lower than for the control samples. These results indicate that the enzymetreated samples are more tender. The lower standard deviation for the enzyme-treated meat shows a more uniform texture exists in those samples than in the control samples. This reduced textural variation suggests a greater degree of enzymatic action on tougher meat. Similarly, the lower stiffness value and lower standard deviation for the enzyme treated meat demonstrates that these samples were more tender and had more textural uniformity than the control samples.

The experimental results indicated that in addition to the tenderizing effects of the proteolytic enzymes upon meats, the water absorbing capacity of freeze dried meats is increased. Therefore, the use of proteolytic enzymes derived from a fungal enzyme preparation would improve the rate and completeness of rehydratability of such meats.

These results, coupled with the ease with which the fungal enzymes can be readily and cheaply produced, suggest that fungal enzymes constitute a potentially useful source of enzyme for meat processing. Although in Example 4 the meat to which the enzyme was applied was flaked and formed beef steak, the enzyme may be applied to whole meat by soaking the meat in a solution containing the enzyme or by injection of a solution of the enzyme. The enzyme may also be injected into an animal prior to slaughter to allow for circulation through the animal's tissues.

We claim:

1. A method of tenderizing meat muscle with a proteolytic enzyme obtained by the culturing of *Trichoderma reesei* strain MCG80 upon a growth medium containing an inducer of proteolytic enzyme synthesis comprising adding a proteolytically effective amount of said enzyme to meat muscle.

2. A method of tenderizing meat muscle according to claim 1 wherein said *Trichoderma reesei* strain MCG80 is incubated at about pH 3.5 upon a growth medium containing lactose and glucose.

3. A method of tenderizing meat muscle according to claim 2 wherein said meat muscle comprises flaked and formed beef steaks with a proteolytic enzyme content of about 1 gram enzyme per 10 pounds of said beef steak.

4. A method of increasing the water absorbing capacity of stored freeze-dried meats comprising mixing into said freeze dried meat a fungal enzyme preparation obtained from *Trichoderma Reesei* strain MCG80, said preparation including a proteolytic enzyme.

5. A method according to claim 4 wherein said fungal enzyme preparation has been obtained by culturing *Trichoderma reesei* strain MCG80 at pH 3.5 on a growth medium containing lactose and glucose.

6. A method according to claim 5 wherein said fungal enzyme preparation has been purified by acetone fractionation and further purified by affinity chromatography.

* * * * *